(12) United States Patent
Ames et al.

(10) Patent No.: US 7,103,946 B2
(45) Date of Patent: Sep. 12, 2006

(54) METHOD AND APPARATUS FOR MAKING AN ABSORBENT COMPOSITE

(75) Inventors: Todd Ames, York, SC (US); Ricky Lee Kenley, Charlotte, NC (US); Bobby R. Lomax, Fort Mill, SC (US)

(73) Assignee: Celanese Acetate LLC, Charlotte, NC (US)

( * ) Notice: Subject to any disclaimer, the term of this patent is extended or adjusted under 35 U.S.C. 154(b) by 300 days.

(21) Appl. No.: 10/672,109

(22) Filed: Sep. 26, 2003

(65) Prior Publication Data
US 2005/0066494 A1    Mar. 31, 2005

(51) Int. Cl.
*D02J 1/18*    (2006.01)
*D02J 3/18*    (2006.01)
(52) U.S. Cl. .......................................... 28/282; 28/220
(58) Field of Classification Search .................. 28/282, 28/283, 271, 278, 221, 267, 219, 220, 245, 28/246, 247, 258; 26/99, 105, 101, 104; 19/66 T, 66 R, 65 T, 65 R, 66.2, 66.1; 264/210.8, 264/211.14, 211.15, 46.1; 156/180, 441, 156/166
See application file for complete search history.

(56) References Cited

U.S. PATENT DOCUMENTS

| | | | | |
|---|---|---|---|---|
| 3,017,309 A | * | 1/1962 | Crawford et al. ............ | 156/161 |
| 3,032,829 A | * | 5/1962 | Mohoney et al. ............ | 19/65 T |
| 3,079,663 A | * | 3/1963 | Dyer et al. .................. | 156/178 |
| 3,095,343 A | * | 6/1963 | Berger ......................... | 156/180 |
| 3,156,016 A | * | 11/1964 | Dunlap et al. ............... | 19/66 T |
| 3,226,773 A | | 1/1966 | Paliyenko | |
| 3,262,181 A | * | 7/1966 | Hawkins et al. ............. | 28/283 |
| 3,328,850 A | * | 7/1967 | Watson ........................ | 19/65 T |
| 3,546,722 A | * | 12/1970 | Watson ........................ | 5/636 |
| 3,796,035 A | * | 3/1974 | Watson ........................ | 57/239 |
| 3,960,645 A | * | 6/1976 | Brackmann et al. ......... | 156/441 |
| 4,468,845 A | * | 9/1984 | Harris ........................... | 28/283 |
| 4,522,616 A | * | 6/1985 | Hyde et al. ................... | 493/44 |
| 5,203,757 A | * | 4/1993 | Kampen ....................... | 493/44 |
| 5,331,976 A | | 7/1994 | St.Pierre | |
| H1565 H | | 7/1996 | Brodof et al. | |
| 6,068,620 A | | 5/2000 | Chmielewski | |
| 6,253,431 B1 | | 7/2001 | Ames et al. | |
| 6,543,106 B1 | | 4/2003 | Ames et al. | |
| 2003/0105442 A1 | | 6/2003 | Johnston et al. | |
| 2003/0114814 A1 | | 6/2003 | Baker et al. | |

(Continued)

FOREIGN PATENT DOCUMENTS

JP    60-26537    10/1982

OTHER PUBLICATIONS

U.S. Appl. No. 09/219,818, filed Dec. 23, 1998, Ames et al.

(Continued)

*Primary Examiner*—Amy B. Vanatta
(74) *Attorney, Agent, or Firm*—Hammer & Hanf,P.C.

(57) ABSTRACT

A method and apparatus for making an absorbent composite from continuous tow is disclosed. The method and apparatus includes the steps of or means for spreading a crimped tow; de-registering the crimped tow; shaping the de-registered tow to a substantially rectangular cross-section; and distributing a particulate onto the shaped tow. The step of or means for de-registering the crimped tow uses at least two pairs of rollers, each pair of rollers having a metal-faced roller and a rubber-face roller. The metal-faced rollers are oppositely disposed between the pair of rollers. Alternatively, the metal-faced rollers are disposed between the pair of rollers on the same side.

34 Claims, 7 Drawing Sheets

U.S. PATENT DOCUMENTS

| | | |
|---|---|---|
| 2003/0130638 A1 | 7/2003 | Baker |
| 2003/0132762 A1 | 7/2003 | Delzer et al. |
| 2003/0134559 A1 | 7/2003 | Delzer et al. |
| 2003/0135176 A1 | 7/2003 | Delzer et al. |
| 2003/0135177 A1 | 7/2003 | Baker |
| 2003/0135178 A1 | 7/2003 | Hasen |
| 2003/0143324 A1 | 7/2003 | Delzer et al. |
| 2003/0150551 A1 | 8/2003 | Baker |

OTHER PUBLICATIONS

U.S. Appl. No. 10/671,904, filed Sep. 26, 2003, Ames et al.
U.S. Appl. No. 10/672,036, filed Sep. 26, 2003, Ames et al.
U.S. Appl. No. 10/672,519, filed Sep. 26, 2003, Ames et al.
U.S. Appl. No. 10/672,673, filed Sep. 26, 2003, Ames et al.
U.S. Appl. No. 10/672,674, filed Sep. 26, 2003, Ames et al.

* cited by examiner

METHOD AND APPARATUS FOR MAKING AN ABSORBENT COMPOSITE

FIELD OF THE INVENTION

The invention is directed to a method and apparatus for making an absorbent composite from a continuous tow.

BACKGROUND OF THE INVENTION

An absorbent composite is a component of a disposable absorbent garment. Such garments include, but are not limited to, infant diapers or training pants, adult incontinence products, and feminine hygiene products. Typically, the absorbent composite comprises mixtures of fibrous material (e.g., wood pulp or fluff) and a superabsorbent polymer (SAP) that are sandwiched between strata, such as tissues, nonwovens, and permeable and impermeable films.

It is known to use continuous tow in the manufacture of absorbent composites. See Japanese Kokoku 60-26537, US SIR H1565, and U.S. Pat. Nos. 6,068,620; 6,253,431; and 6,543,106. Each is discussed below.

Japanese Kokoku 60-26537 discloses an absorbent structure made of crimped acetate tow and pulverized pulp but no SAP. Referring to FIG. 4, the process for making the absorbent structure is shown. Tow is removed from a bale and is spread by an air banding jet 14. The tow is then de-registered between roller pairs 16, 17. The de-registered tow is further spread and given a uniform density by a second air jet 18. Pulverized pulp 21 is spread on to opened tow after it leaves the second air jet. Thereafter, absorbent sheets are added and the absorbent pad is folded into its final form.

U.S. Statutory Invention Registration H1565 discloses an absorbent structure made of crimped acetate tow and SAP that is preferably adhered to the opened tow by a binder. The tow is opened with a Korber & Co. Model AF2 machine (a common machine used in the manufacture of cigarette filters) and subsequently a mixture of binder and SAP or binder then SAP is added to the tow.

U.S. Pat. No. 6,068,620 discloses an absorbent core made of fibrous crimped acetate tow and SAP between an upper and lower layer. Referring to FIG. 7, SAP is added to the tow via a mixing chamber.

U.S. Pat. Nos. 6,253,431 and 6,543,106 disclose a method of making an absorbent structure from crimped acetate tow and SAP. Referring to FIG. 1, tow from a bale is spread by a banding jet 130. The tow is then partially de-registered (or opened) through the roller assemblies 40, 64, 70. Each roller assembly has a metal roller 42, 62, 72 and a rubber roller 44, 64, 74. Optimally, a liquid is applied to the opened tow by liquid additive assembly 80. The tow is-then further opened, shaped in air jet 240. Solid substances, such as SAP, are added after the fully opened and shaped tow emerges from jet 240. Solid substances are added via a vibratory feeder.

There is, however, a need for more practical processes and apparatus to make an absorbent composite.

SUMMARY OF THE INVENTION

A method and apparatus for making an absorbent composite from continuous tow is disclosed. The method and apparatus includes the steps of or means for spreading a crimped tow; de-registering the crimped tow; shaping the de-registered tow; and distributing a particulate onto the shaped tow. The step of or means for de-registering the crimped tow uses at least two pairs of rollers, each pair of rollers having a metal-faced roller and a rubber-face roller. The metal-faced rollers are oppositely disposed between the pair of rollers. Alternatively, the metal-faced rollers are disposed between the pair of rollers on the same side.

DESCRIPTION OF THE DRAWINGS

For the purpose of illustrating the invention, there is shown in the drawings a form that is presently preferred; it being understood, however, that this invention is not limited to the precise arrangements and instrumentalities shown.

FIGS. 1, 1a, and 1b are schematic views of the present invention.

DETAILED DESCRIPTION OF THE INVENTION

Figure 1:
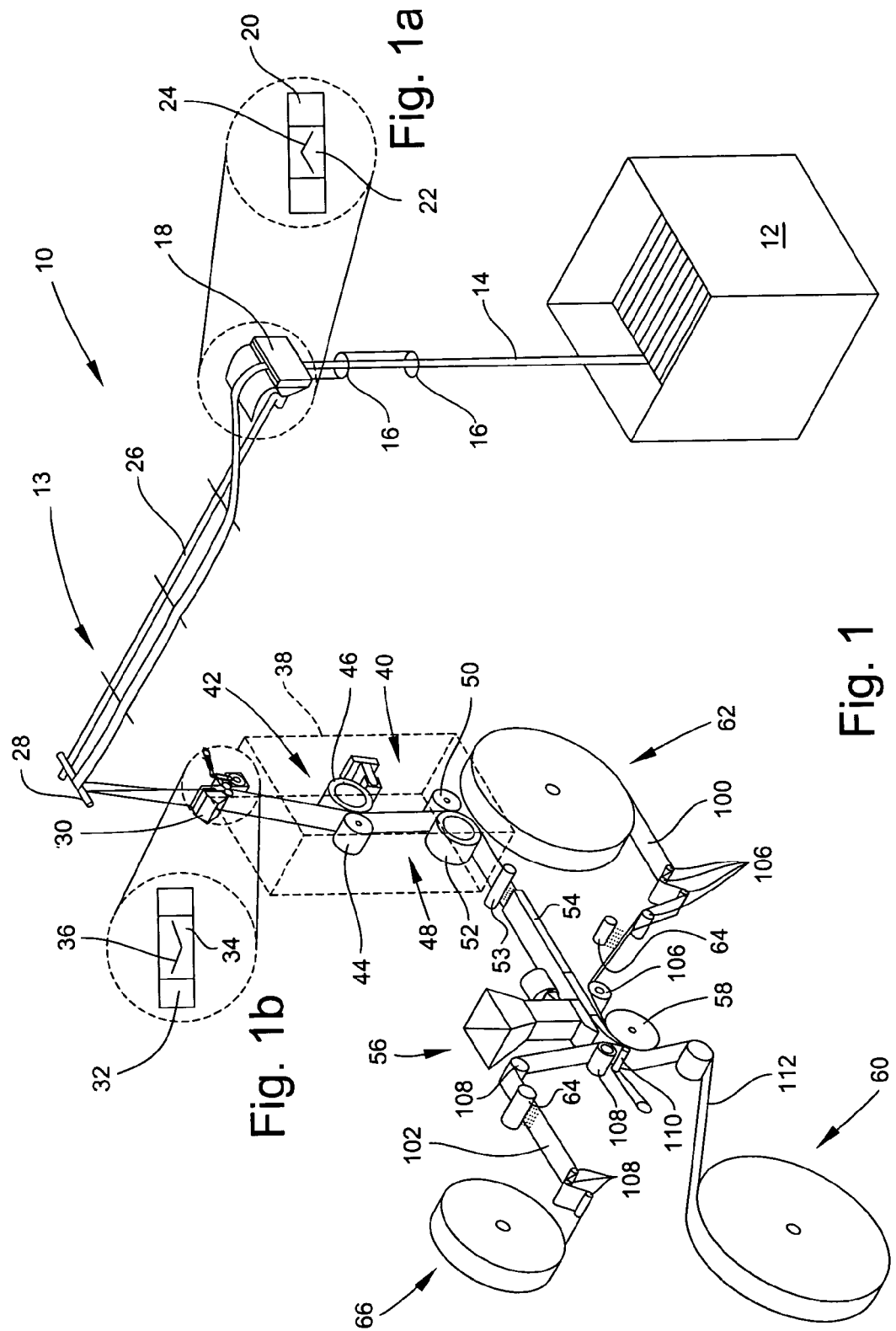

Referring to the drawings wherein like numerals indicate like elements, there is shown in FIG. 1 an apparatus 10 for making an absorbent composite from a continuous tow.

The absorbent composite discussed herein is for use in manufacture of absorbent garments. Absorbent garments include, for example, diapers or training pants, adult incontinence products, and feminine hygiene products. The absorbent composites disclosed herein are particularly useful in the absorbent cores and garments disclosed in U.S. Patent Publications Nos. 2003/0105442; 2003/0114814; 2003/0135177; and 2003/0135178, each is incorporated herein by reference.

Tow is a large strand of continuous manufactured fiber filaments without definite twist, collected in a loose, band- or rope-like form, usually held together by crimp. Suitable tows materials include, but are not limited to, polyolefins, polyesters, polyamides, cellulosics, and mixtures thereof. Of these, cellulosic fibers are preferred. Cellulosic fibers include rayon, acetate (cellulose acetate), and triacetate (cellulose triacetate) fibers. Acetate tow is most preferred. For example, an acetate tow may consist of about 2,500 to about 25,000 fibers having an individual denier of from about 1 to about 15, preferably from 2 to 10, and most preferably 3 to 8. The total denier of a single acetate tow band may range from about 2,500 to about 125,000, preferably 15,000 to 75,000, and most preferably 20,000 to 40,000. The tow is preferably crimped, with about 5 to about 40 crimps per inch (2 to 16 crimps per cm), preferably, 25 to 30 crimps per inch (10 to 12 crimps per cm). The fibers of the tow may have any cross-sectional shape, including 'y,' 'x,' round, crenulated, dog bone or combinations thereof. The tow may include a finish, the finish comprising about 0.3% to about 5% by weight of the tow, preferably, 0.5 to 2.0%. The tow's cross-sectional dimensions may range from about 25 mm to 100 mm in width, preferably, 40 to 60 mm, and about 1 to 10 mm in height, preferably 2 to 5 mm. Tows are commercially available and are delivered in compressed bales.

Figure 2:
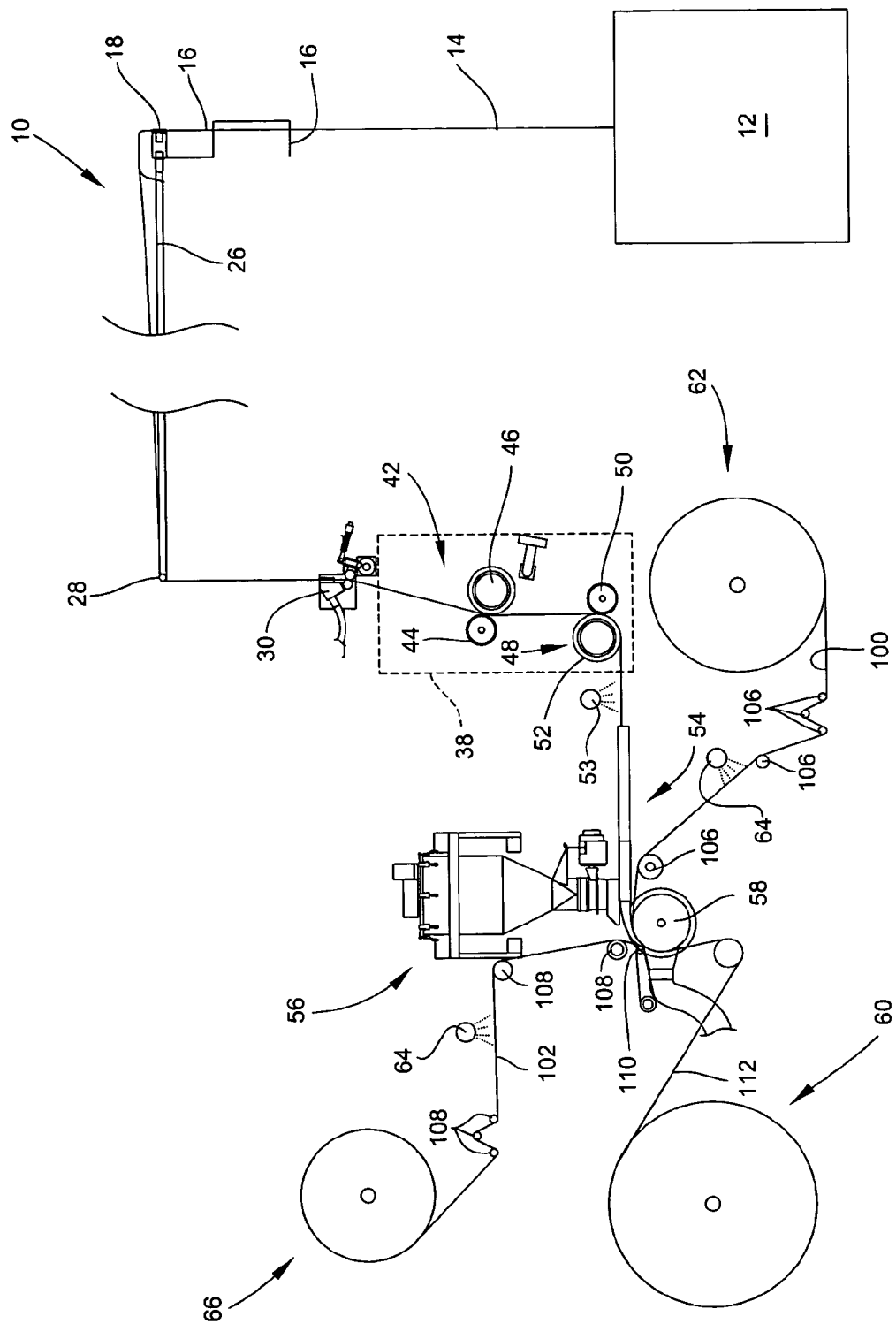
FIG. 2 is an elevational view of the present invention.

In FIGS. 1 and 2, there is shown an apparatus 10 for making absorbent composites from a continuous tow. Apparatus 10 generally comprises: apparatus 13 for spreading the tow, i.e., increasing its width from its compressed state in the bale; a de-registering apparatus 40 for de-registering the crimped fibers of the tow; a tow shaping apparatus 54 for forming the tow into its desired cross-sectional shape; a particle distribution apparatus 56 whereby particulate matter, e.g., SAP, may be delivered to the shaped tow, and a wind-up station 60 where the particulate laden, shaped tow is sandwiched between strata and then wound-up. Wind-up may be eliminated and the absorbent composite may be run directly into a subsequent machine for formation into the ultimate absorbent garment (for example, see: U.S. Patent Publications Nos. 2003/0105442; 2003/0114814; 2003/0134559; 2003/0135177; 2003/0135178; 2003/0150551, each is incorporated herein by reference).

Bale 12 is preferably located at a right angle to the travel of the tow through the de-registering apparatus 40, tow shaping apparatus 54, and particulate distribution apparatus 56. The bale may be located at any location, including a position inline with the foregoing apparatus. However, location at the right angle is preferred to allow easy access to the bale for changing out depleted bales and to allow easier visual inspection of the tow by an operator.

Tow 14 is delivered to spreading apparatus 13 from bale 12. Apparatus 13 guides between two locations and spreads the tow. Spreading apparatus 13 preferably has at least two banding jets. These banding jets work to spread and stabilize the tow as it moves through the rest of apparatus 10. Tow 14 is drawn from bale 12 and guided through rings 16 to a first banding jet 18. Banding jet 18 is a device that is used to spread (i.e., increase the width) and stabilize the tow 14. Banding jet 18, see FIG. 1a, generally comprises a plate 20 having a channel 22 with an air nozzle 24 located within channel 22. Any conventional banding jet may be used, for example see U.S. Pat. No. 3,226,773 or U.S. patent application Ser. No. 09/219,818 filed Dec. 23, 1998, both are incorporated herein by reference. Air nozzle 24 is shown as a chevron, however, other shapes or patterns are permissible, for example, slots can be replaced by holes. The chevron may have a width of 50–140 mm. Compressed air is blown through air nozzle 24 and partially spreads the tow. The pressure of the compressed air may range from 0.5 to 5.0 psig, preferably, 2.5–3.0 psig. The width of channel 22 is referred to as $W_1$.

Tow carrier structure 26 carries tow 14 leaving banding jet 18 over the distance from jet 18 to the rest of apparatus 10. Guide roller 28, located at the distal end of carrier 26, re-orients the tow for entry into the rest of the apparatus 10.

Second banding jet 30 receives tow 14 from guide roller 28. The second banding jet 30, FIG. 1b, comprises a plate 32 having a channel 34 with an air nozzle 36. Any conventional banding jet may be used, for example see U.S. Pat. No. 3,226,773 or U.S. patent application Ser. No. 09/219,818 filed Dec. 23, 1998, both are incorporated herein by reference. Air nozzle 36 is shown as a chevron, however, other shapes or patterns are permissible, for example, slots can be replaced by holes. The chevron may have a width of 70–155 mm. Compressed air is blown through air nozzle 36 and partially spreads the tow. The pressure of the compressed air may range from 0.5 to 5.0 psig, preferably, 3.0–3.5 psig. Channel 34 has a width $W_2$. Preferably, $W_1$ is less than $W_2$.

Cabinet 38 (shown in phantom) contains de-registering apparatus 40 that receives tow 14 from spreading apparatus 13. Cabinet 38 acts as a shielding device to prevent contaminates such as adhesives from gumming up or fouling the roll surfaces of the de-registering apparatus 40 and as a safety device. While cabinet 38 is preferred, other means can be used to accomplish the shielding function, such as, for example, curtains, air curtains, wire cages. Cabinet 38 will be discussed in greater detail below.

Figure 2A:
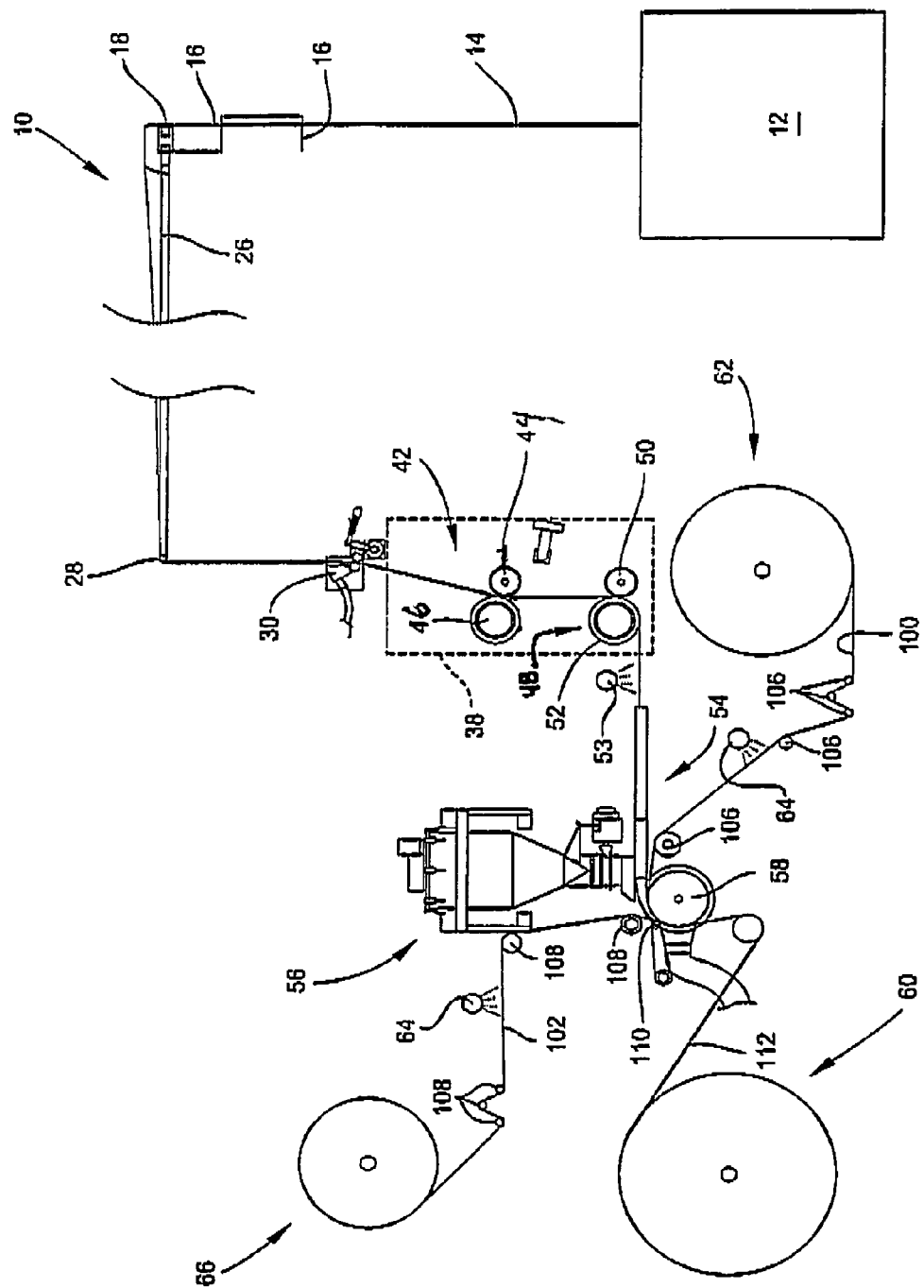
FIG. 2a is an elevational view of another embodiment of the present invention.

De-registering apparatus 40, which is preferably contained within cabinet 38, has at least two pairs of rollers 42 and 48. In de-registration, the individual crimped filaments of the tow are de-registered (or opened) and prepared for shaping. Roller pair 42 has a metal-faced roller 44 and a rubber-faced roller 46 (rubber-faced refers to any elastic polymer). Roller pair 48 also has a metal-faced roller 50 and a rubber-faced roller 52 (rubber-faced refers to any elastic polymer). The metal-faced rollers are driven and have diameters of 160 mm. The rubber-faced rollers have diameters of 250 mm. The pair of rollers 42 and 48 may be vertically oriented (as shown), horizontally oriented, or at some angle therebetween. Metal-faced rollers 42 and 50 may be smooth, grooved, threaded, textured, or combinations thereof. When grooved or threaded, the ratio of open surface to flat surface may nominally range from 90:10 to 10:90, preferably with 25:75; 50:50; and 75:25, and most preferred, 75:25. The rubber-faced rollers are preferably placed opposite one another in the pairing as shown, but they may be disposed on the same side (FIG. 2a), preferably on the side closest to apparatus 54, so that fibers in the tow do not foul in the open surface of the metal rollers. The nip pressure between each roller pairs 42 and 48 is two (2) bars with a 70 mm diameter pressure cylinder. The roller pair 48 has greater surface speed than roller pair 42. When cellulose acetate tow is used, the ratio of roller speed for pair 48 ($S_{48}$) to pair 42 ($S_{42}$) may range from $1 \leq S_{48}/S_{42} \leq 2$, and $S_{48}/S_{42}$ is preferably 1.1–1.7, and most preferred 1.3–1.4.

Optionally, a liquid application station 53 located after de-registration apparatus 40 may be used. Such liquids may be used to, for example, facilitate binding of fibers in the tow or particulate to the tow, or deodorize or scent the absorbent composite, or add an anti-microbial agent to the composite, or alter the hydrophilicity of the tow. Such liquids include water, hydrophilic liquids (such as alcohols, glycols, dimethyl sulfide, ketones, ethers and the like), plasticizers (such as triacetin), surfactants, and solutions containing plasticizers, surfactants and the like. Liquid application station 53 may include spray nozzles, disk applicators, rotating brush applicators, wick contact rolls, and the like, as is known in the art.

Tow shaping apparatus 54 receives the tow 14 from de-registering apparatus 40. Tow shaping apparatus 54 is used to shape the opened tow into a predetermined cross-sectional shape, preferably a generally rectangular cross-section, for use in the absorbent garment. Other cross-sectional shapes are also possible, they include: circular, oval, square, channeled, and grooved. A preferred tow shaping apparatus 54 is illustrated in, for example, U.S. Pat. No. 6,253,431, incorporated herein by reference. Another tow shaping apparatus 54 is illustrated in U.S. Pat. No. 5,331,976, incorporated herein by reference. When tow-shaping apparatus 54 has a 70 mm width, banding jet 18 has a width ($W_1$) of 62.5 mm and banding jet 30 has a width ($W_2$) of 65 mm. When apparatus 54 has a width of 110, $W_1$ is 82.5 mm and $W_2$ is 108 mm. When apparatus 54 has a width of 120, $W_1$ is 102.5 mm and $W_2$ is 118 mm. Additionally, apparatus 54 includes a dancer (not shown) that controls the thickness of the shaped tow as it exits apparatus 54. The dancer is preferably a plate pivotally mounted within apparatus 54 and adapted to have bearing engagement with the tow along the tow's width. The dancer controls the thickness of the tow to ensure uniform thickness of the tow and to enable the line speeds disclosed hereinafter. The dancer is also illustrated in U.S. Patent Publications 2003/0130638; 2003/0135176; 2003/0143324, each is incorporated herein by reference.

Particulate distribution apparatus 56 is located at the distal end of tow shaping apparatus 54. Particulate distribution apparatus 56 is used to distribute particulate in a predetermined manner onto and/or into the opened, shaped tow and will be discussed in greater detail below. Particulate particularly includes SAP, but also includes other solid materials, such as adhesives, fragrances, wood pulp, deodorizers, anti-microbial agents, and the like. Particulate distribution apparatus 56 is further described in U.S. Patent Publications Nos. 2003/0130638; 2003/0132762; 2003/0135176; and 2003/0143324, each is incorporated herein by reference.

Wind-up apparatus 60 is used to sandwich the particulate laden, shaped tow between strata (for example, tissues, nonwovens, and permeable and non permeable films). Apparatus 60 is conventional and driven. Strata 100 from unwind apparatus 62 is fed through a plurality of guide rollers 106 and passed by an adhesive applicator 64 to a vacuum apparatus 58. Adhesive applicator 64 may be any adhesive applicator, but preferably is a hot melt adhesive applicator. Vacuum applicator 58 is coupled to a vacuum source 104 (see FIG. 4) and may be any suitable vacuum apparatus, such as a vacuum drum or vacuum table (also see: U.S. Patent Publication No. 2003/0134559, incorporated herein by reference). Vacuum pressures range from 3–6 inches of water, preferably 5 inches of water. The vacuum drum or vacuum table is, preferably, driven. Strata 102 from unwind apparatus 66 is fed through a plurality of guide rollers 108 and passed by another adhesive applicator 64 to vacuum apparatus 58. At vacuum apparatus 58, stratum 100 and 102 sandwich the particulate laden, shaped tow. Strata 102 is pressed into the other layers by a lay on roller 110. Lay on roller 110 may include a cavity of channel 114 (see FIG. 5) to shape the absorbent composite 112 into a predetermined shape (e.g., hour glass, rectangular, etc.) and/or press stratum together for sealing. Thereafter, absorbent composite 112 may be wound-up on wind-up apparatus 60 or fed directly to a machine for making an absorbent garment.

The line speed, as measured at the vacuum drum 58, is preferably greater than 190 m/min, preferably greater than 225 m/min, and most preferably greater than 250 m/min. The maximum line speed is about 300 m/min. The ratio of tow speed exiting from cabinet 38 to the line speed at the vacuum drum 58 is greater than 1 and less than 3, preferably between 1.8 to 3.0, and most preferably about 2.4. This allows accumulation of the tow in the tow shaping apparatus 54. Additionally, line speed can be used to control particulate distribution apparatus 56. Coupling line speed to apparatus 56 minimizes particulate (e.g., SAP) loss during ramp up and ramp down of apparatus 10.

Additionally, static elimination devices (not shown) may be placed in apparatus 10 adjacent the tow band to decrease static charges that may accumulate on the tow band. Placement of those devices is within the skill of the art. Further, the driven rollers are preferably coupled or controlled (not shown) in a conventional manner to facilitate start-up, shutdown, and vary line speeds during operation.

Figure 3:
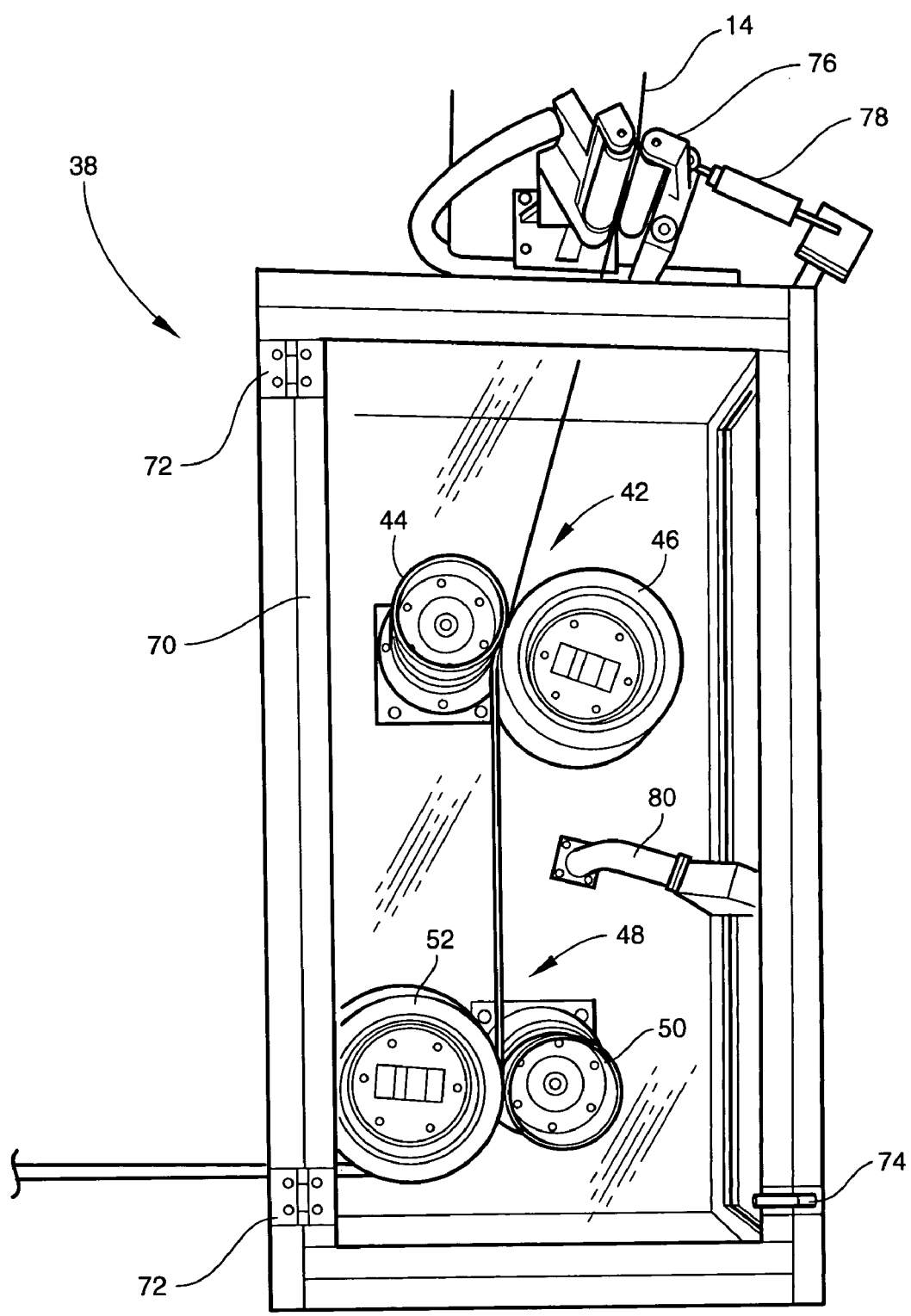
FIG. 3 is an elevational view of the de-registration mechanism of the present invention.

In FIG. 3, cabinet 38 is shown in greater detail. Tow 14 prior to entering cabinet 38 engages guide rollers 76. Guide rollers 76 may be opened and closed via an opening mechanism 78. Guide rollers 76 have a diameter of 50 mm and exert a nip pressure ranging from 0.5–5 bar, preferably 2–2.5 bar (using a 1.0625 inch cylinder). Cabinet 38 includes a door 70 that is fastened to the rest of the cabinet via hinges 72 and may be fastened shut by latch 74. Cabinet 38 encloses de-registering apparatus 40 and prevents contaminants, such as adhesives from adhesive applicator 64 from fouling the surface of the rollers. Fouling of the surfaces can cause adhesion of the tow to the rolls. Cabinet 38 is supplied with an air nozzle 80 that is used to provide positive pressure within cabinet 38 so that contaminants cannot enter. The positive pressure may range from 0.1–1.0 psig, preferably 0.25–0.5 psig.

Figure 4:
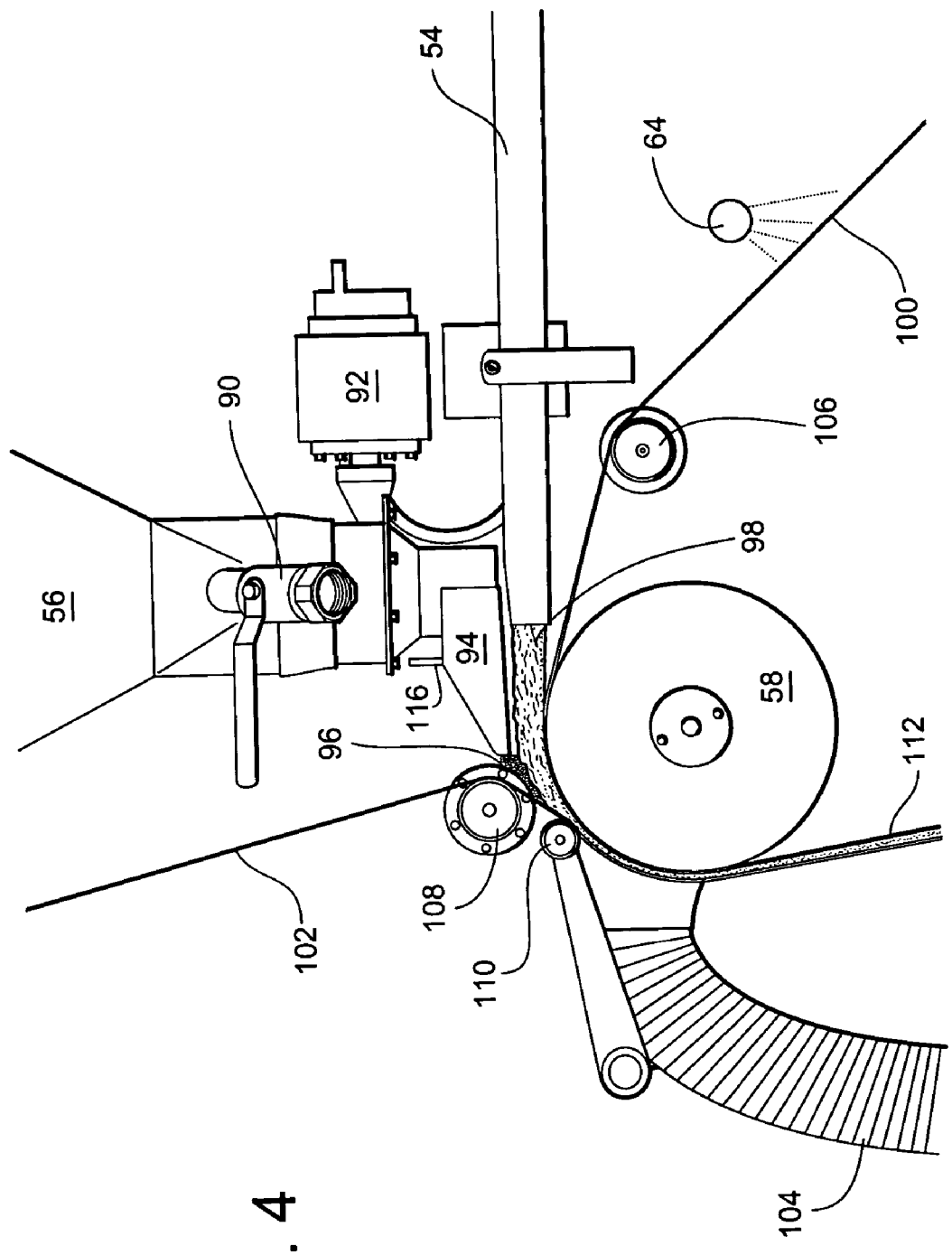
FIG. 4 is an elevational view of the shaping and particulate distribution mechanisms of the present invention.
Figure 5:
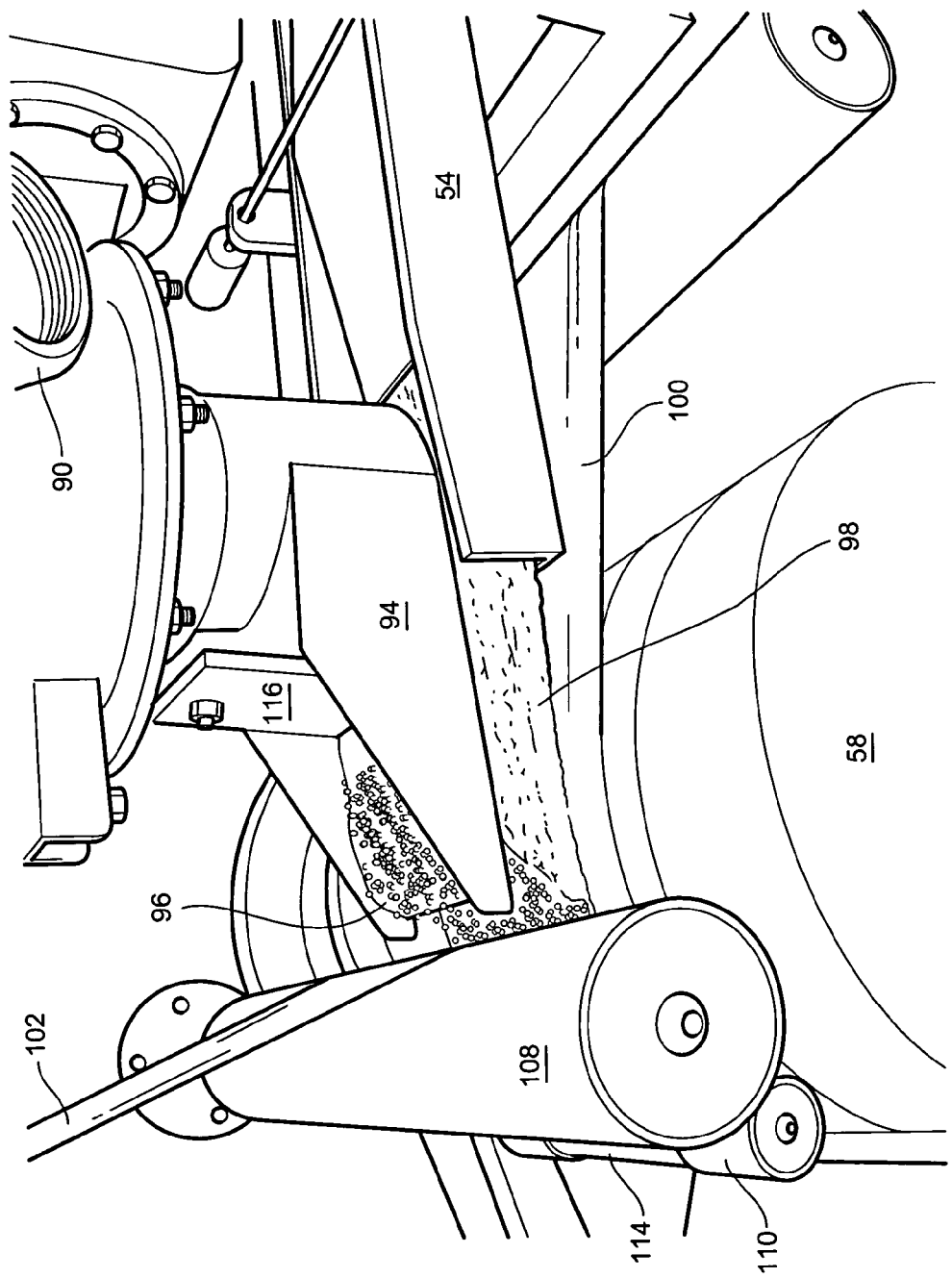
FIG. 5 is an isometric view of the particulate distribution mechanism of the present invention.
Figure 6:
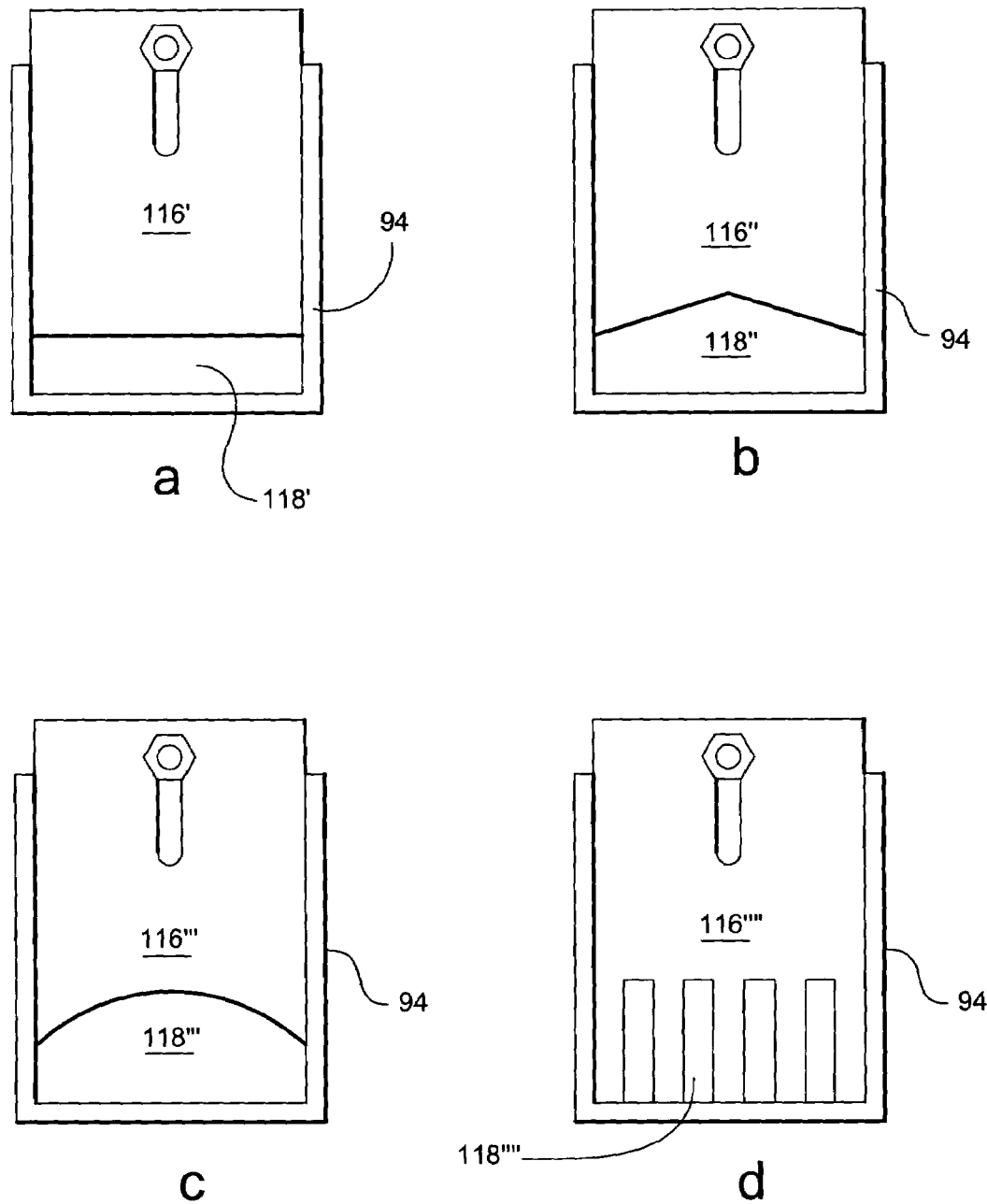
FIGS. 6a, 6b, 6c, and 6d are elevational views of a portion of the particulate distribution mechanism of the present invention.

Referring to FIGS. 4, 5, and 6, the operation of the particulate distribution apparatus 56 is illustrated in greater detail. Particulate distribution apparatus 56 is preferably a vibratory feeder. At the bottom of a hopper is a clean out valve 90 and a motor 92 drives the feeder. Particulate is vibrated through an orifice defined, in part, by a trough 94 where it is deposited onto opened tow 98. Particulate, when SAP, may be fed at rates of 1–25 Kg/min, preferably 5–13.5 Kg/min, assuming garment formation of 500–900/min with 10–15 g/garment. Particulate 96 and shaped tow 98 are held in place by the vacuum apparatus 58 (a rotary vacuum drum is shown), while stratum 100 and 102 are applied thereto. Stratum 100 and 102 are guided to vacuum apparatus 58 by rollers 106 and 108, respectively. Adhesive from applicators 64 is preferably applied to the stratum prior to arrival at the vacuum apparatus 58. When the stratum sandwich the particulate laden, shaped tow, on vacuum apparatus 58, the lay on roller 110 squeezes the composite to seal it shut, preferably with the lateral edges of the stratum being sealed together. Thereafter, absorbent composite 112 is wound-up or directed on into a subsequent absorbent garment making operation.

The distribution of the particulate is controlled, in part, by an orifice 118, FIG. 6. Orifice 118 is defined by trough 94 and plate 116 that may be moved to open and close the orifice. In FIG. 6, four possible configurations of orifice 118 are illustrated. Orifice 118', FIG. 6a, illustrates a rectangular shaped orifice. Orifice 118", FIG. 6b, illustrates a triangularly shaped orifice. Orifice 118''', FIG. 6c, illustrates an arcuate shaped orifice. Orifice 118'''', FIG. 6d, illustrates a serrated or toothed shaped orifice. Of course, other configurations for the orifice would be obvious to those of ordinary skill in the art.

The present invention may be embodied in other forms without departing from the spirit and the essential attributes thereof, and, accordingly, reference should be made to the appended claims, rather than to the foregoing specification, as indicated the scope of the invention.

That which is claimed:

1. A method for making an absorbent composite from a continuous tow comprising the steps of:
   spreading a crimped tow;
   de-registering the crimped tow by using at least two pairs of rollers, each pair of rollers having a metal-faced roller and a elastic-polymer-faced roller and the metal-faced rollers being oppositely disposed about the tow;
   shaping the de-registered tow; and
   distributing a particulate onto the shaped tow.

2. The method of claim 1 wherein said metal faced rollers being smooth, grooved, threaded, textured, or combinations thereof.

3. The method of claim 1 wherein said elastic-polymer faced roller being smooth.

4. The method of claim 1 wherein said pair of rollers being vertically aligned, one over the other.

5. The method of claim 1 wherein one said pair of rollers ($S_f$) rotates faster than the other pair of rollers ($S_a$).

6. The method of claim 5 wherein a speed ratio ($S_f/S_a$) being in the range of $1 \leq S_f/S_a \leq 2$.

7. The method of claim 6 wherein the speed ratio ($S_f/S_a$) being in the range of $1.1 \leq S_f/S_a \leq 1.7$.

8. The method of claim 1 further comprising shaping the de-registered tow to a substantially rectangular cross-section.

9. The method of claim 1 further comprising applying a liquid to the tow.

10. An apparatus for making an absorbent composite from a continuous tow comprising:
   means for spreading a crimped tow;
   means for de-registering the crimped tow by using at least two pairs of rollers, each pair of rollers having a metal faced roller and a elastic-polymer faced roller and the metal faced rollers being oppositely disposed about the tow;
   means for shaping the de-registered tow; and
   means for distributing a particulate onto the shaped tow.

11. The apparatus of claim 10 wherein said metal faced rollers being smooth, grooved, threaded, textured, or combinations thereof.

12. The apparatus of claim 10 wherein said elastic-polymer faced roller being smooth.

13. The apparatus of claim 10 wherein said pair of rollers being vertically aligned, one over the other.

14. The apparatus of claim 10 wherein one said pair of rollers ($S_f$) rotates faster than the other pair of rollers ($S_a$).

15. The apparatus of claim 14 a speed ratio ($S_f/S_a$) being in the range of $1 \leq S_f/S_a \leq 2$.

16. The apparatus of claim 15 wherein the speed ratio ($S_f/S_a$) being in the range of $1.1 \leq S_f/S_a \leq 1.7$.

17. The apparatus of claim 10 further comprising means for shaping the de-registered tow to a substantially rectangular cross-section.

18. The apparatus of claim 10 further comprising means for applying a liquid to the tow.

19. A method for making an absorbent composite from a continuous tow comprising the steps of:
   spreading a crimped tow;
   de-registering the crimped tow by using at least two pairs of rollers, each pair of rollers having a metal-faced roller and a elastic-polymer-faced roller, the metal faced rollers being oppositely disposed about the tow, and said pairs of rollers being vertically aligned, one said pair over the next said pair or at any angle between vertically aligned and horizontally aligned, but not including horizontally aligned;
   shaping the de-registered tow; and
   distributing a particulate onto the shaped tow.

20. The method of claim 19 wherein said metal faced rollers being smooth, grooved, threaded, textured, or combinations thereof.

21. The method of claim 19 wherein said elastic-polymer faced roller being smooth.

22. The method of claim 19 wherein one said pair of rollers ($S_f$) rotates faster than the other pair of rollers ($S_a$).

23. The method of claim 22 wherein a speed ratio ($S_f/S_a$) being in the range of $1 \leq S_f/S_a \leq 2$.

24. The method of claim 23 wherein the speed ratio ($S_f/S_a$) being in the range of $1.1 \leq S_f/S_a \leq 1.7$.

25. The method of claim 19 further comprising shaping the de-registered tow to a substantially rectangular cross-section.

26. The method of claim 19 further comprising applying a liquid to the tow.

27. An apparatus for making an absorbent composite from a continuous tow comprising:
   means for spreading a crimped tow;
   means for de-registering the crimped tow by using at least two pairs of rollers, each pair of rollers having a metal faced roller and a elastic-polymer faced roller, the metal faced rollers being oppositely disposed about the tow, and said pairs of rollers being vertically aligned, one said pair over the next said pair or at any angle between vertically aligned and horizontally aligned, but not including horizontally aligned;
   means for shaping the de-registered tow; and
   means for distributing a particulate onto the shaped tow.

28. The apparatus of claim 27 wherein said metal faced rollers being smooth, grooved, threaded, textured, or combinations thereof.

29. The apparatus of claim 27 wherein said elastic-polymer faced roller being smooth.

30. The apparatus of claim 27 wherein one said pair of rollers ($S_f$) rotates faster than the other pair of rollers ($S_a$).

31. The apparatus of claim 30 wherein a speed ratio ($S_f/S_a$) being in the range of $1 \leq S_f/S_a \leq 2$.

32. The apparatus of claim 31 wherein the speed ratio ($S_f/S_a$) being in the range of $1.1 \leq S_f/S_a \leq 1.7$.

33. The apparatus of claim 27 further comprising means for shaping the de-registered tow to a substantially rectangular cross-section.

34. The apparatus of claim 27 further comprising means for applying a liquid to the tow.

* * * * *